US00PP14260P39

(12) United States Plant Patent
Jones

(10) Patent No.: US PP14,260 P3
(45) Date of Patent: Nov. 4, 2003

(54) NEMESIA PLANT NAMED 'PENVAL'

(50) Latin Name: *Nemesia*
Varietal Denomination: Penval

(76) Inventor: Sidney James Jones, PenHow Nursery, Carron Hill, St. Bridges, Netherwent Magor Caldicot, South Wales (GB)

( * ) Notice: Subject to any disclaimer, the term of this patent is extended or adjusted under 35 U.S.C. 154(b) by 0 days.

(21) Appl. No.: 10/035,304

(22) Filed: Dec. 28, 2001

(65) Prior Publication Data

US 2003/0126656 P1 Jul. 3, 2003

(51) Int. Cl.[7] ..... A01H 5/00

(51) Int. Cl.[7] ..... A01H 5/00

(52) U.S. Cl. ..... Plt./263

(58) Field of Search ..... Plt./263

*Primary Examiner*—Kent Bell

(57) ABSTRACT

A new and distinct cultivar of Nemesia plant named 'Penval' that is characterized by compact habit, narrow green leaves, upright fragrant flower spikes and a floriferous display of pink-purple flowers. In combination these characteristics set 'Penval' apart from all other existing varieties of Nemesia known to the inventor.

2 Drawing Sheets

Genus/species: Nemesia hybrid.
Denomination: 'Penval'.

BACKGROUND OF THE INVENTION

The present invention relates to a new and distinct cultivar of Nemesia plant known botanically as Nemesia hybrid and that will be referred to hereinafter by the cultivar name 'Penval'.

The new Nemesia is a product of a planned breeding program conducted by the Inventor in Netherwent, Wales. The breeding program objectives were to improve upon well-known varieties such as *Nemesia denticulata* 'Confetti' (unpatented), *Nemesia caerulea* 'Innocence' (unpatented), *Nemesia caerulea* 'Joan Widler' (unpatented), *Nemesia caerulea* 'Woodcote' (unpatented), and *Nemesia caerulea* 'Elliott's' (unpatented). The goals of the breeding program were to improve on plant habit by breeding plants that were more compact, with stiff, upright flower spikes, increase the size of the flower and the length of flowering time, improve the color range by producing clear colors, and produce plants that root readily and consistently from vegetative stem cuttings.

The new Nemesia originated from a cross-pollination made by the Inventor in 1996 of an unnamed and unpatented Nemesia hybrid, as the female, or seed, parent with an unnamed and unpatented Nemesia hybrid, as the male, or pollen, parent. The cultivar 'Penval' was discovered and selected by the Inventor as a plant within the progeny from this cross-pollination in a controlled environment in Netherwent, Wales, in 1996.

'Penval' is distinguishable from the parent plants by compact growth habit, narrowness of leaves, uprightness of spikes, number of flower spikes, size of flower and pink-purple flower color. 'Penval' is distinguishable from all other Nemesia known to the Inventor by the flower size and flower color.

'Penval' was first asexually propagated by the Inventor in 1997 in a cultivated area or Netherwent, Wales using vegetative stem cuttings and has shown that the unique features of this new Nemesia plant are stable and reproduced true to type in successive generations of asexual reproduction.

SUMMARY OF THE INVENTION

The following traits have been repeatedly observed and represent the distinguishing characteristics of 'Penval'. In combination these traits set the new cultivar apart from all other existing varieties of Nemesia known to the inventor. 'Penval' has not been tested under all possible conditions and phenotypic differences may be observed with variations in environmental, climatic, and cultural conditions, however, without any variance in genotype.

1. Nemesia 'Penval' exhibits a compact habit.
2. Nemesia 'Penval' flowers profusely and exhibits fragrant pink-purple flowers.
3. Nemesia 'Penval' exhibits an abundance of flower spikes, uniquely colored flowers and large flowers for the pink color category of Nemesia.
4. Nemesia 'Penval' exhibits stiff, upright flower spikes.
5. Nemesia 'Penval' exhibits narrow green leaves.
6. Nemesia 'Penval' is hardy to minus 5° Centigrade.

BRIEF DESCRIPTION OF THE DRAWINGS

The accompanying color drawings illustrate the overall appearance of the new Nemesia cultivar 'Penval' showing the colors as true as it is reasonably possible to obtain in colored reproductions of this type. Colors in the drawings may differ from the color values cited in the detailed botanical description, which accurately describe the actual colors of the new variety 'Penval'. Drawings were made of plants that were 12-months-old and grown in two-litre containers under greenhouse conditions in Encinitas, California.

The drawing on sheet 1 illustrates the entire plant and habit from a side perspective.

The drawing on sheet 2 is a close-up view of the flowers.

The drawings were made using conventional photographic techniques and although colors may appear different from actual colors due to light reflectance, they are as accurate as possible by conventional photography and laser printing techniques.

BOTANICAL DESCRIPTION OF THE PLANT

The following is a detailed description of the Nemesia plant named 'Penval'. Data was collected in Arroyo Grande, Calif. from 12-month-old plants grown in two-litre containers under greenhouse conditions. Phenotypic differences may be observed with variations in environmental, climatic, and cultural conditions. The color determinations are in accordance with The Royal Horticultural Society Colour Chart except where general color terms of ordinary dictionary significance are used. Growing requirements are similar to other Nemesia plants.

Botanical classification: Nemesia 'Penval'.
Species: hybrid.
Common name: Nemesia.
Use: Bedding and patio plant.
Parentage: The parent of Nemesia 'Penval' are unnamed Nemesia hybrids.
- *Female parent.*—Unnamed Nemesia hybrid.
- *Male parent.*—Unnamed Nemesia hybrid.

Propagation: Vegetative stem cuttings.
Sexuality: Hermaphrodite.
Growth Habit: Compact habit.
Plant dimensions: 40 cm. in height and 50 cm. in width in a 2-litre container.
Type: Hardy perennial.
Time to initiate roots: Approximately 16 days at temperatures of 21° Centigrade are needed to produce rooted cuttings.
Crop time: 12 months are required to produce a finished two-litre from a rooted cutting.
Root system: Numerous and fine.
Hardiness: Hardy to minus 5° Centigrade.
Disease and pest susceptibility: There are no disease problems known to the inventor other than what affects typical Nemesia.
Stem:
- *Stem shape.*—Quadrilateral.
- *Stem length.*—28 cm. in length.
- *Stem diameter.*—2 mm. in diameter.
- *Stem surface.*—Stipitate glandular.
- *Stem color.*—138B.
- *Stem texture.*—Flexible with corner ridges and occasional flexuous stems.
- *Internode length.*—2–8 cm. between nodes.
- *Branching habit.*—Ascending and freely branching.

Foliage:
- *Leaf shape.*—Lanceolate.
- *Leaf division.*—Simple.
- *Apex.*—Acute.
- *Base.*—Rounded.
- *Margins.*—Closest to crenate.
- *Surface.*—Glabrous.
- *Arrangement.*—Opposite.
- *Leaf length.*—2 cm. in length.
- *Leaf width.*—1 cm. in width.
- *Leaf color* (*adaxial surface*).—138A.
- *Leaf color* (*abaxial surface*).—138B.
- *Attachment.*—Petiolate.
- *Petiole dimensions.*—1 mm. in length and less than 0.50 mm. in diameter.
- *Petiole color* (*adaxial surface*).—138A.
- *Petiole color* (*abaxial surface*).—138B.
- *Vein pattern.*—Prominent mid-vein depressed on adaxial surface and protruding on abaxial surface.
- *Vein color.*—138B.

Flowers:
- *Flowering season.*—Spring and summer.
- *Fragrance.*—Sweet scent.
- *Self-cleaning or persistent.*—Self-cleaning.
- *Inflorescence dimensions.*—8 cm. in length and 3 cm. in width.
- *Type of inflorescence.*—Terminal racemes.
- *Quantity of flowers.*—Floriferous. Approximately 15 flowers per peduncle.
- *Peduncle dimensions.*—12 cm. in length and 1 mm. in diameter.
- *Pedicel dimensions.*—6 mm. in length and less than 1 mm. in width.
- *Peduncle surface.*—Glabrous.
- *Pedicel surface.*—Stipitate glandular.Peduncle color: 138B.
- *Pedicel color.*—138C.
- *Bud shape.*—Oval.
- *Bud color.*—155A.
- *Bud dimensions.*—3 mm. in diameter and 5 mm. in length.
- *Flower shape.*—Personate.
- *Flower dimensions.*—16 mm. in length, 1.50 cm. at the widest part and 0.50 cm. in depth.
- *Palate color.*—16A.
- *Nectary color.*—163A.
- *Nectary dimensions.*—3 mm. in width and 2 mm. in length.
- *Palate dimensions.*—3 mm in length and 2 mm. in width.
- *Surface.*—Glabrous.
- *Lip margin.*—Entire.
- *Lip apex* (*upper and lower*).—Each lobe on each lip has a rounded apex.
- *Lip base* (*upper and lower*).—The base of each lip is truncate.
- *Number of lips.*—Two in number, one single with 2 slight lobes and one with 4 lobes.
- *Upper lip color* (*abaxial and adaxial surfaces*).—A combination of 78A, 78B and 78C are present on the individual upper lip. In addition there are dark markings of 89A where the upper lip meets the palate of the lower lip.
- *Lower lip color* (*abaxial and adaxial surfaces*).—A combination of 78C and 78D are present on the individual lower lip. In addition there are darker markings of 89A to the right and left of the palate.
- *Throat color* (*inside*).—89D.
- *Throat color* (*outside*).—89D.
- *Dark markings on flower.*—89A.
- *Upper lip surfaces* (*adaxial and abaxial*).—Glabrous.
- *Lower lip surfaces* (*adaxial and abaxial*).—Glabrous.
- *Upper lip dimensions.*—1.5 cm. in width and 1 cm. in length.
- *Lower lip dimensions.*—8 mm. in width and 6 mm. in length.
- *Number of lobes* (*upper lip*).—Four in number.
- *Lobe dimensions* (*upper lip*).—Each lobe is 4 mm. in width and 1 cm. in length.

*Number of lobes* (*lower lip*).—Two slight lobes.
*Lobe dimensions* (*lower lip*).—4 mm. in width and 6 mm. in length.
*Flower spur dimensions.*—6 mm. in length and 1 mm. in diameter.
*Spur color.*—1D.
*Calyx dimensions.*—3 mm. in length and 4 mm. in width.
*Sepals.*—Five in number.
*Sepal surface.*—Stipitate glandular.
*Sepal apex.*—Acute.
*Sepal margin.*—Entire.
*Sepal color* (*adaxial surface*).—138A.
*Sepal color* (*abaxial surface*).—138A.
*Lastingness of individual flower.*—Flower lasts 7–10 days.

Reproductive organs:
*Stamens.*—Four in number and didynamous.
*Color of stamens.*—155A.
*Stamen dimensions.*—1 mm. in length and less than 0.25 mm. in diameter.
*Anther color.*—8B.
*Amount of pollen.*—Moderate.
*Pollen color.*—8A.
*Anther dimensions.*—Less than 0.50 mm. in length and less than 0.50 mm. in width.
*Pistil.*—One.
*Pistil color.*—155A.
*Pistil dimensions.*—0.50 mm. in length and 0.50 mm. in diameter.
*Ovary dimensions.*—1 mm. in length and 2 mm. in width.
*Ovary shape.*—Oval.
*Ovary position.*—Superior.
*Ovary color.*—145B.

Seed production:
*Quantity of seed.*—Approximately 15 fertile seeds per capsule.
*Capsules.*—Approximately 20 capsules per flowering spike, but this is markedly influenced by how many times the plant is pinched back.
*Capsule dimensions.*—12 mm. in length and 7 mm. in width.
*Capsule color.*—177D.
*Capsule surface.*—Glossy.
*Appearance of seed.*—Flattened and winged.
*Seed color.*—200D and wing 156D.
*Shape of seed.*—Oval.
*Seed dimensions.*—3 mm. in length and 2.5 mm, in width.

I claim:

1. A new and distinct cultivar of Nemesia plant named 'Penval' as described and illustrated herein.

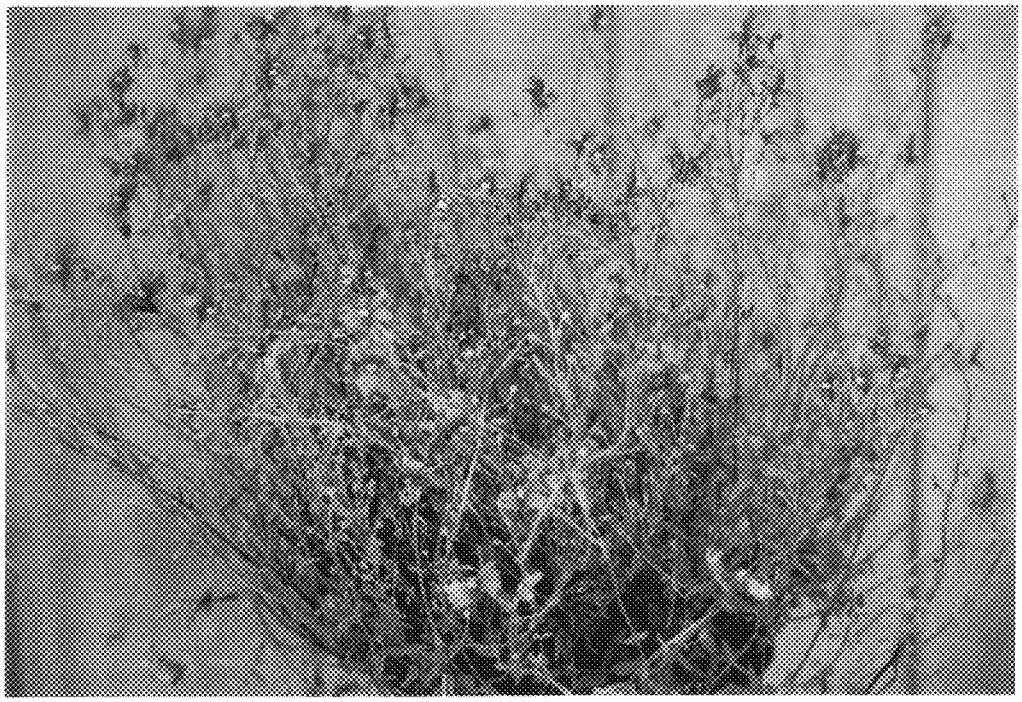

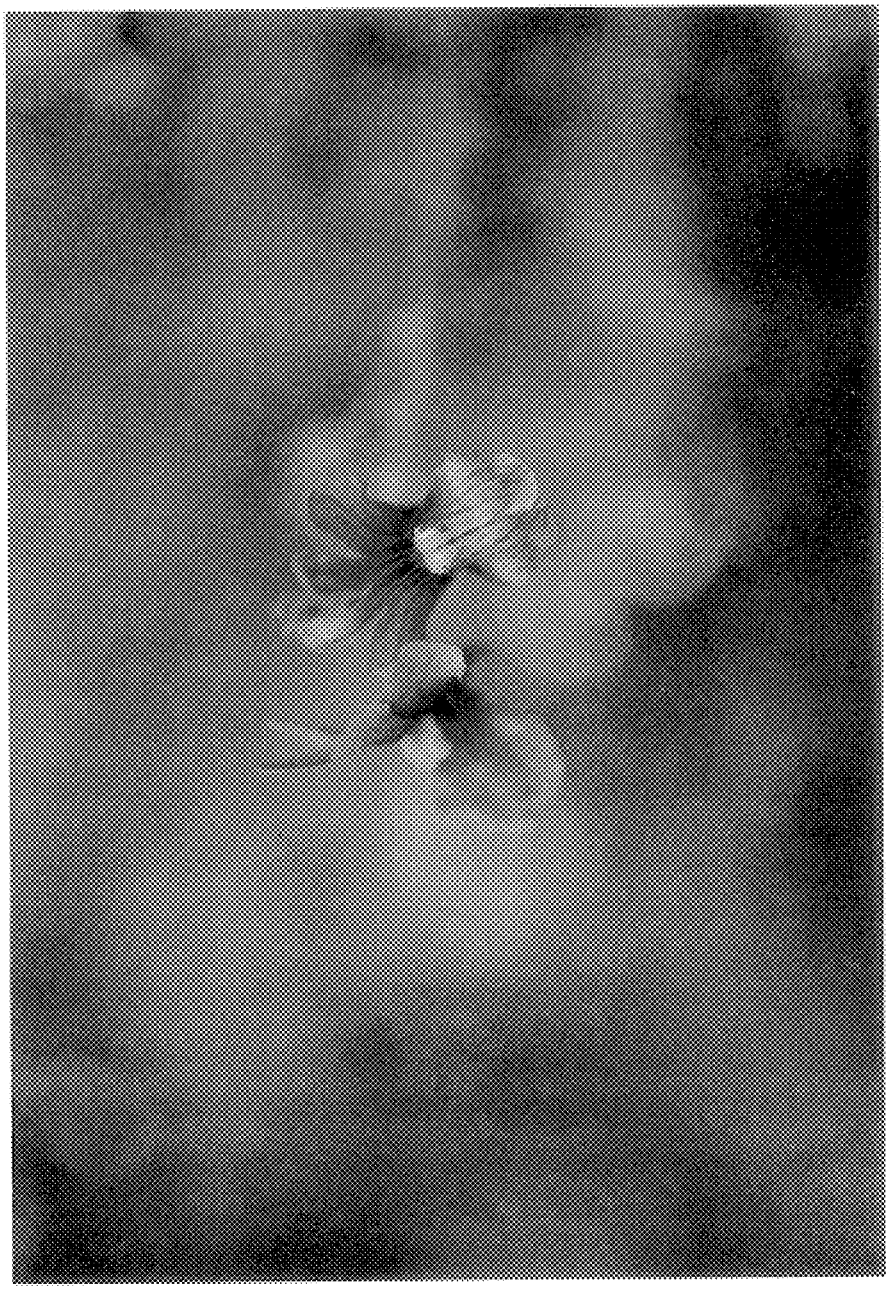

* * * * *